United States Patent [19]

Dolive

[11] 3,930,726
[45] Jan. 6, 1976

[54] SYSTEM FOR MEASURING VOLUMETRIC RATIOS OF LIQUID SUSPENDED SOLIDS

[75] Inventor: Stephen E. Dolive, Orlando, Fla.

[73] Assignee: Reginald C. Shuck, Orlando, Fla.; a part interest

[22] Filed: May 29, 1974

[21] Appl. No.: 474,354

[52] U.S. Cl. ............... 356/39; 356/205; 356/206; 356/208
[51] Int. Cl.² ........................................ G01N 33/16
[58] Field of Search ............ 356/39, 204, 205, 206, 356/208; 326/71 R

[56] References Cited
UNITED STATES PATENTS

| | | | |
|---|---|---|---|
| 3,684,450 | 8/1972 | Adler et al. | 356/39 X |
| 3,740,143 | 6/1973 | Groner et al. | 356/39 |
| 3,817,632 | 6/1974 | Picunko et al. | 356/39 |
| 3,830,569 | 8/1974 | Meric | 356/39 |

Primary Examiner—R. V. Rolinec
Assistant Examiner—Darwin R. Hostetter
Attorney, Agent, or Firm—Duckworth, Hobby & Allen

[57] ABSTRACT

A system for determining the volumetric ratio of solids suspended in a liquid comprises a photometer or similar means for passing a beam of electromagnetic energy through a sample of the liquid having solids suspended therein. Means for measuring a characteristic representative of the amount of energy absorbed by the sample is provided, as a photo detector for example. The volumetric ratio is then computed by applying a proportionality factor characteristic of the solids suspended in the liquid to the output of the measuring means.

22 Claims, 4 Drawing Figures

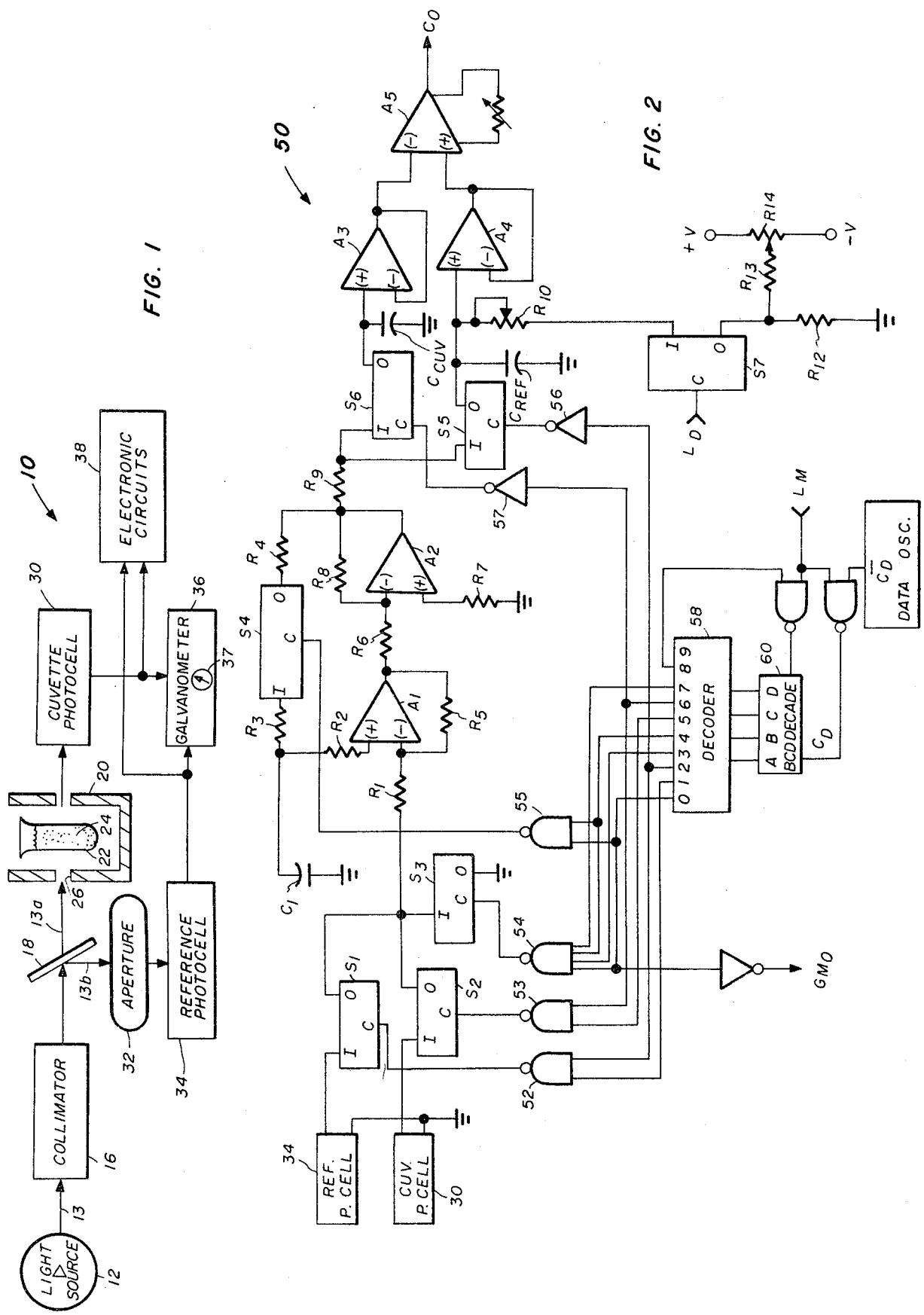

SYSTEM FOR MEASURING VOLUMETRIC RATIOS OF LIQUID SUSPENDED SOLIDS

BACKGROUND OF THE INVENTION

1. Field of the Invention

The present invention relates to systems and methods for determining the volumetric ratio of liquid suspended solids with respect to the suspending liquid. In particular, the present invention relates to systems and methods for measuring "hematocrit", which is the percent ratio of blood cells per unit of whole blood.

2. Description of the Prior Art

Hematocrit is defined as packed blood cell volume, generally expressed as a percent per 100 milliliters of whole blood.

Hematocrit is one of several laboratory determinations with respect to red blood cells in human blood, or the blood of other animals. Two other allied determinations are that of red blood cell count per cubic milliliter and hemoglobin, which is expressed as grams per 100 milliliters. To a hematologist, computations of ratios involving these three determinations are of considerable value.

The first of these ratios is the mean corpuscular volume (MCV) which is determined by multiplying hematocrit by 10 and dividing the result by the red blood cell count expressed in millions per cubic millimeter, such that MCV is expressed in cubic microns. This ratio approximates red blood cell (erythrocyte) size.

The second ratio is the mean corpuscular hemoglobin (MCH) which is determined by multiplying hemoglobin by 10 and dividing the result by blood cell count expressed in millions per cubic millimeters, such that MCH measurements are expressed in micromicrograms. This ratio approximates the hemoglobin per cell by weight.

The third ratio is the mean corpuscular hemoglobin concentration (MCHC), which is determined by multiplying hemoglobin by 100 and dividing the result by the hematocrit. This ratio is expressed in percent, and approximates hemoglobin concentration in red blood cells by volume. Of these three ratios (MCV, MCH, and MCHC), only MCH may be calculated without knowledge of the hematocrit.

Hematocrit has traditionally been determined in the laboratory by centrifuging small tubes of blood in order to pack the cells in the bottom of the tubes. Results obtained in this manner, which is referred to as microhematocrit, vary as between centrifuges and operators.

Automated equipment for measuring hematocrit fall into two categories. One such arrangement employs the centrifuging techniques discussed previously, with automatic loading, unloading and interpretation.

The second type of automated hematocrit measuring system involves electronic processing of signals obtained by measuring conductivity in proportion to cell size when a dilute solution of cells is passed between two electrodes. Examples of this type of arrangement are described in U.S. Pat. Nos. 3,692,410 to Jurany et al. and 3,439,267 to Coulter et al.

In addition, other types of automated blood analyzing systems are commercially available which are not capable of determining hematocrit. Many of these systems utilize photometry techniques, whereby a characteristic of the amount of light absorbed by a blood sample is processed to determine red blood cell count and hemoglobin.

Other systems and techniques for analyzing the volumetric or particulate ratio of liquid suspended particles are disclosed in the following U.S. Pat. Nos.: 3,740,143 to Groner et al.; 3,646,352 to Bol et al.; 2,775,159 and 3,045,123 to Frommer. Carr, in U.S. Pat. No. 3,714,444, discloses a reflective light measuring system employing a logarithmic ratio converter for providing a single output representative of the concentration of suspended solids.

With respect to the measurement of MCV, Stevens, in U.S. Pat. No. 3,084,591, discloses a system for measuring this characteristic. Pelavin, in U.S. Pat. No. 3,634,868 teaches an automatic calibration circuit useful in fluid sampling systems.

SUMMARY OF THE INVENTION

The present application contemplates a system for determining volumetric ratios of solids suspended in a liquid, comprising means for passing a beam of electromagnetic energy through a sample of a liquid having solids suspended therein, means for measuring a characteristic representative of the amount of said energy absorbed by said sample, and means for computing said volumetric ratio by electronically applying a proportionality factor to an output of said measuring means.

A method for determining the hematocrit ratio of blood, which method is incorporated in the system of the present invention, is disclosed in a U.S. patent application entitled HEMATOCRIT MEASURING METHOD, Ser. No. 474,170 filed on an even date with this application by Reginald Shuck. An essential aspect of the teachings of Shuck is the recognition that the hematocrit ratio is directly proportional to the amount of light absorbed by blood cells in a quantity of diluted blood.

An adjunct to the system of the present invention is the inclusion of means for correction of amplifier voltage errors.

DRAWINGS

FIG. 1 is a block diagram illustrating an arrangement of apparatus employed with the present invention.

FIG. 2 is a schematic circuit diagram of a portion of the apparatus shown in FIG. 1.

Figure 3:
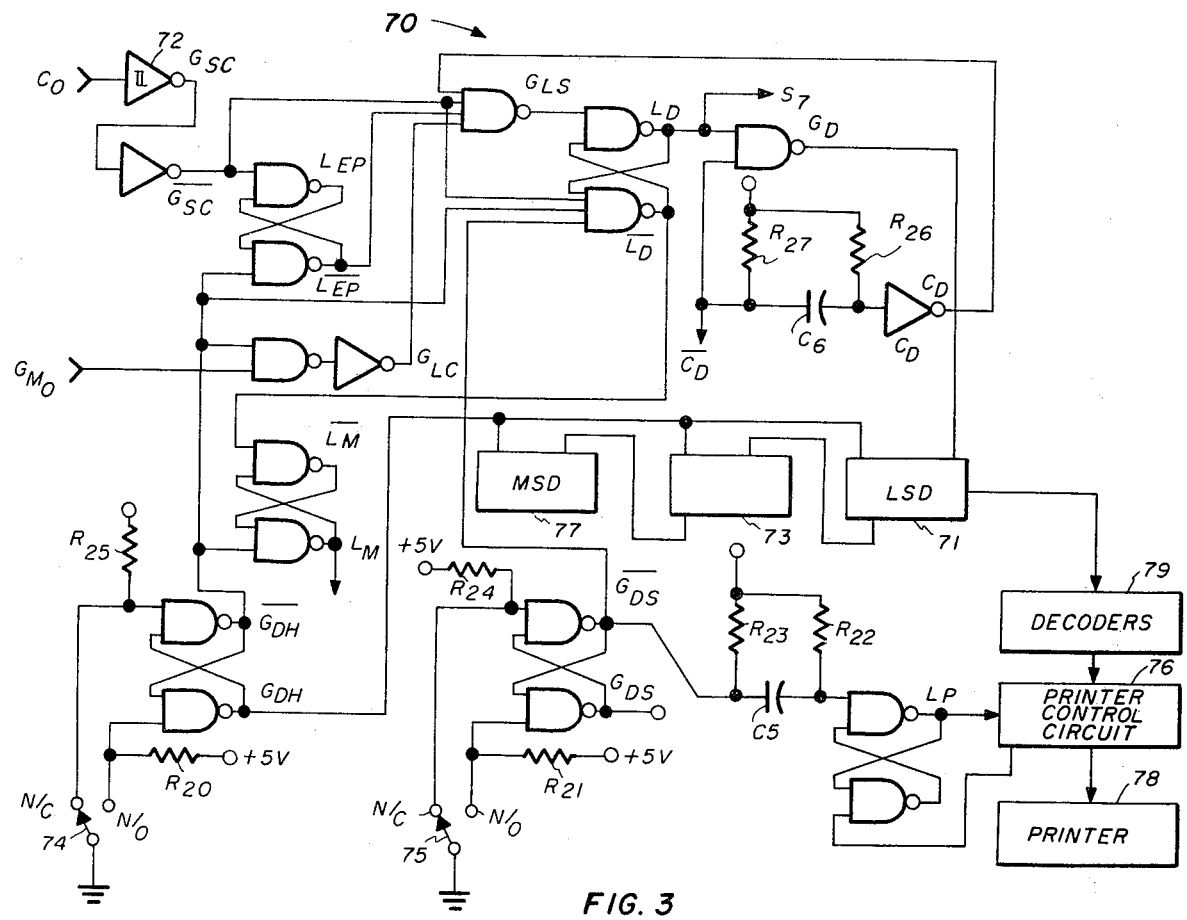
FIG. 3 is another schematic circuit diagram of a portion of the apparatus of FIG. 1.

FIGS. 4(a), (b), (c) and (d) are diagrams illustrating voltages and switching sequences of the circuits shown in FIGS. 2 and 3.

DETAILED DESCRIPTION

A. Method

A method for determining the hematocrit ratio of whole blood will now be described with reference to the apparatus shown in FIG. 1.

The apparatus of FIG. 1 includes a photometer, referred to generally as 10, having a monochromatic light source 12 for producing a light beam 13 along the beam path. The photometer 10 may also include a beam collimator 16 if required. It will be understood by those skilled in the art that various other light source arrangements may also be employed. For example, a non-monochromatic light source may be employed in combination with filtering means to produce a monochromatic output. Suitably, the light in the beam 13 is of a color which is complementary to the color of blood. For example, a green or blue color source is believed suitable.

The photometer 10 may further include a beam splitter 18 for directing one-half of the energy in the beam (identified at 13b) normal to the remainder of the beam 13a. A suitable enclosure 20 is provided for holding a blood sample container (cuvette) 22, which contains a diluted blood sample 24 the hematocrit ratio of which is to be measured. Preferably, the blood 24 is diluted with a physiological saline solution to a consistency suitable for determining hematocrit. This saline solution may comprise sodium chloride using a concentration on the order of 0.85%.

The enclosure 20 further includes suitable apertures 26, 28 aligned with the source 12 so as to allow the beam portion 13a to pass through the cuvette 22, the diluted blood sample 24 and thereafter impinge upon a photocell 30, which detects the amount of light in the beam portion 13a transmitted through the blood sample. Again, it will be understood by those familiar with the optics art that a wide variety of optical techniques may be used to provide a light beam through the cuvette 22 which is balanced with respect to a reference portion of the beam, as with the one embodiment described next.

The split portion of 13b of the beam 13 is suitably directed through an adjustable aperture 32 and then impinges on a reference photocell 34, which detects the amount of light energy in the split beam portion 13b. Signals representative of the light detected by each photocell 30, 34, is then fed into a galvanometer 36, which compares the signal levels from the two photo cells and displays, usually with a deflecting needle meter 37, the percent of light transmitted through the blood sample 24 with respect to the light energy in the split beam portion 13b. Alternatively, the meter 37 may be calibrated in absorbance, which is a measurement of the amount of light absorbed by the blood cells in the sample 24 with respect to the amount of light which would be passed through the cuvette 22 without the presence of the blood sample (as represented by the energy in split beam portion 13b). The relationship between absorbance and transmission is given by the expression:

$$\text{Abs.} = 2 - \log_{10} T \qquad (1)$$

where:
- Abs. = Absorbance;
- $T$ = per cent of light passing through sample with respect to the incident light.

The photometer 10 described thus far is essentially similar to a class of commercially available photometers generally referred to as colorimeters, which have been widely employed in the measurement of hemoglobin. Another class of photometers, referred to as spectrophotometers, may likewise be employed with this method. Spectrophotometers are more complex than colorimeters, and usually include a diffraction grating through which the light beam is passed to produce a spectrum. The output of the diffraction grating is then mechanically and optically manipulated, resulting in a beam of light at a carefully calibrated wavelength and band width.

Again noting FIG. 1, the outputs of the photocells 30, 34 may be transmitted to an electronic circuit 38, an embodiment of which is described below under Section B.

In accordance with the method incorporated in the present invention, the hematocrit ratio of the blood sample 24 is determined as directly related to either the transmission or absorbance characteristics of the light passing therethrough. The hematocrit ratio is expressed with respect to absorbance as follows:

$$HCT = K(\text{Abs.}) \qquad (2)$$

where:
- $HCT$ = unknown hematocrit of sample under test;
- Abs. = amount of light absorbed by sample;
- $K$ = proportionality factor Alternatively, combining expressions 1 and 2 above, the hematocrit of the sample 24 is expressed with respect to the transmission characteristics as follows:

$$HCT = K(2 - \log_{10} T) \qquad (3)$$

In accordance with the above-described teachings of Shuck, the proportionality factor K in expressions 2 and 3 above is given by:

$$(4) \quad K = \frac{HCT_s}{\text{Abs.}_s}$$

where:
- $K$ = proportionality factor
- $HCT_s$ = hematocrit ratio of a standard blood sample measured by any known technique;
- $\text{Abs.}_s$ = the amount of light absorbed by the standard blood sample.

Thus, in order to determine the proportionality factor K, the hematocrit ratio of a standard blood sample S is measured by any known technique. Preferably, this is done by the centrifuging (micro hematocrit) technique described above with respect to the prior art. The standard blood sample S is then diluted with a physiological saline solution and placed in the photometer 10 and the absorbance (or transmission) characteristics of that sample S is measured in the manner described above. While the absorbance characteristic of the sample S may be determined on another photometer, it is preferable to employ the same photometer 10 which is used to measure the absorbance of the sample 24, in order to offset any inherent errors between two different photometers.

By employing expressions 2 and 4 above, the unknown hematocrit of the sample 24 is given as:

$$(5) \quad HCT = \frac{HCT_s}{\text{Abs.}_s} \times \text{Abs.}$$

It will be understood that the hematocrit and absorbance of the standard blood sample S need not be measured each time an unknown hematocrit is to be determined. Suitably, the meter 37 of the galvanometer 36 is provided with calibration means which allows a variable K to be incorporated in the meter reading, and then the K is adjusted by occasionally measuring a standard sample: for example, once a day, or whenever a new batch of saline solution is to be used, since the proportionality factor K may vary dependent on differences in such saline solutions. Further, the proportionality factor may vary between photometers, and it therefore is desirable to employ the same photometer for measuring both samples. The electronic circuits 38 may provide means for automatically computing the unknown hematocrit of the sample 24 under test, to provide an automatic printout for visual display of the hematocrit ratio, as is described next.

B. Electronic System

An electronic system useful for measuring the hematocrit ratio of whole blood, as well as volumetric ratios of other liquid-suspended solids, is shown and described with reference to FIGS. 2, 3 and 4, in which FIG. 2 illustrates an embodiment of an amplifier, charge storage and logarithmic conversion circuit, while FIG. 3 illustrates digital circuitry useful with the embodiment of FIG. 2, in which inputs to and outputs from FIG. 2 with respect to FIG. 3 have common designations.

The circuit in FIG. 2 includes capacitors and resistors, as well as integrated amplifiers, electronic switches and digital circuitry all of which are illustrated using symbols well known to those skilled in the electronic art. Each component is identified in FIG. 2 with an appropriate upper case letter, such as capacitor C, resistor R, amplifier A, switches S, and so forth, followed by a lower case reference numeral or letter. While specific values and examples of the circuit components are set forth in the attached Appendix, it will be understood that changes in the circuit values or in the selection of components can be made without departing from the scope of the present invention.

1. Photocell detection and logarithmic conversion

The photocell detection and the logarithmic conversion circuit, referred to generally as 50, is shown in FIG. 2. The circuit 50 includes two electronic switches $S_1$ and $S_2$ which are respectively coupled to the reference photocells 34 and the cuvette photocell 30 (note FIG. 1). The outputs of switches $S_1$ and $S_2$ are both coupled to the inverting input of an operational amplifier $A_1$ through a gain determining resistor $R_1$, and to ground through another switch $S_3$. The output of amplifier $A_1$ is coupled to the inverting input of another operational amplifier $A_2$ through resistor $R_6$. The output of amplifier $A_2$ is coupled back into the non-inverting input of $A_1$ through resistors $R_4$, $R_3$, and $R_2$ through switch $S_4$, to the non-inverting inputs of amplifiers $A_3$ through resistors $R_9$ and switch $S_6$, and to the non-inverting input of amplifier $A_4$, through resistor $R_9$ and switch $S_5$.

The outputs of amplifiers $A_3$ and $A_4$ are coupled to the inverting and non-inverting inputs, respectively, of comparator amplifier circuit $A_5$. Amplifiers $A_3$ and $A_4$ are connected as voltage followers, with the output also fed back into the inverting input thereof.

Reference is again made to amplifiers $A_1$ and $A_2$. Capacitor $C_1$, serving as a stabilizing capacitor, is coupled between the junction of resistors $R_3$ and $R_2$ and to ground. Resistors $R_5$ and $R_8$ are feedback resistors coupled between the respective outputs of amplifiers $A_1$ and $A_2$ to the inverting input thereof. Resistor $R_7$ is coupled between the non-inverting input of amplifier $A_2$ and ground.

Referring to the right hand portion of FIG. 2, a capacitor $C_{cuv}$ is coupled between the output of switch $S_6$ and ground, and another capacitor $C_{ref}$ is coupled between the output of switch $S_5$ and ground. A potentiometer $R_{10}$ having a "wiper" terminal shorted to one side, is coupled across capacitor $C_{ref}$ to switch $S_7$ and resistor $R_{12}$ to ground. Resistor $R_{13}$ is coupled between the output of switch $S_7$ to the wiper of a potentiometer $R_{14}$, which serves as a dropping resistor between the positive and negative terminals of a voltage source.

Each of the switches $S_1 - S_4$, inclusive, are controlled by respective NAND gates 52, 53, 54 and 55. Switches $S_5$ and $S_6$ are controlled by inverters 56 and 57, and switch $S_7$ is controlled from the $L_D$ output of the digital multiplexing circuit, described below. The NAND gates and inverters 52–57, inclusive, are coupled to the 0-7 outputs of a one-out-of ten decoder circuit 58, which is driven by a BCD decade circuit 60. It will be appreciated that the circuits 52–58 are equivalent in function to devices such as programmable read only memories (PROM).

2. Digital Control Circuit

FIG. 3 illustrates a digital circuit, referred to generally as 70, for controlling the circuit 50 of FIG. 2. The circuit 70 includes an inverter Schmitt trigger 72, the input of which is coupled to the output $C_0$ of the comparator $A_5$ of FIG. 2. The circuit 70 further includes two single pole double throw switches 74 and 75, or equivalent means, to initiate operation of the circuits 50 and 70, as described below.

As shown in FIG. 3, there is also included three data registers 71, 73 and 77, two of which registers 71 and 77 are respectively identified as the least significant digit LSD register and the most significant digit MSD register. All three registers 71, 73 and 77 are coupled to decoder circuit 79, which in turn feeds a printer control circuit 76, controlling a printer 78.

The circuit 70 additionally includes a plurality of digital NAND and inverter gates, as well as associated resistors $R_{20} - R_{27}$ and capacitors $C_5$ and $C_6$. Each of these components are depicted by commonly accepted symbols in the drawing. As shown in FIG. 3, these components are coupled to provide outputs thereof as represented by the following symbols:

$C_D$ = Output of comparator $A_5$
$G_{SC}$ = Output from Schmitt trigger 72
$G_{DS}$ = Gate output indicating that N/O contacts of switch 75 are closed
$G_{DH}$ = Gate output indicating that N/O contacts of switch 74 are closed.
$G_{MO}$ = Gate output that is high when the switch multiplexer decoder 58 is in the zero position
$G_D$ = Gate output to data register 71 input
$G_{LC}$ = Logarithmic conversion activation gate
$C_D$ = Output from clock oscillator
$C_{DA}$ = Output gate that generates momentary high pulse when $C_D$ changes state from low to high
$G_{LS}$ = Latch set gate
$L_{EP}$ = Error prevention latch
$L_M$ = Multiplexer control latch
$L_D$ = Data control latch
$L_P$ = Printer control latch The circuit 70 of FIGS. 3 serves to provide clocking and control functions to the circuit 50 of FIG. 2, and it will be recognized by those skilled in the electronic arts that various modifications may be made to the circuit 70 to accomplish this purpose.

3. Operation of System

One cycle of the operation of a system embodying circuits 50 and 70 will now be described.

Initially, the cuvette 22 containing the blood sample 24 under test is placed in the container 20. The switch 74 is then activated, connecting the normally open terminal N/O to ground. This may be done manually, or alternatively, a microswitch or equivalent means may be placed with the container 20 to detect the presence of the cuvette 22. When switch 74 is closed, latch $L_M$ is set by NAND gate $\overline{G_{DH}}$. $\overline{G_{DH}}$ changes to its low state and sets $L_M$ which activates the amplifier system 50. Simultaneously, $L_{EP}$ is reset and $L_D$ is held in its reset condition. The resetting of $L_{EP}$ partially preconditions $G_{LS}$. Thereafter, comparator output $C_o$ and gate output $\overline{G_{SC}}$ are stabilized in their high states, further preconditioning $G_{LS}$ and partially preconditioning $L_D$. $G_{LC}$ is low and prevents the setting of $L_D$ by the pulsing output of $C_{DA}$. The reset inputs to all three data registers decades are held high by $G_{DH}$ thereby entering and maintaining zero in all three decades.

Figure 4:
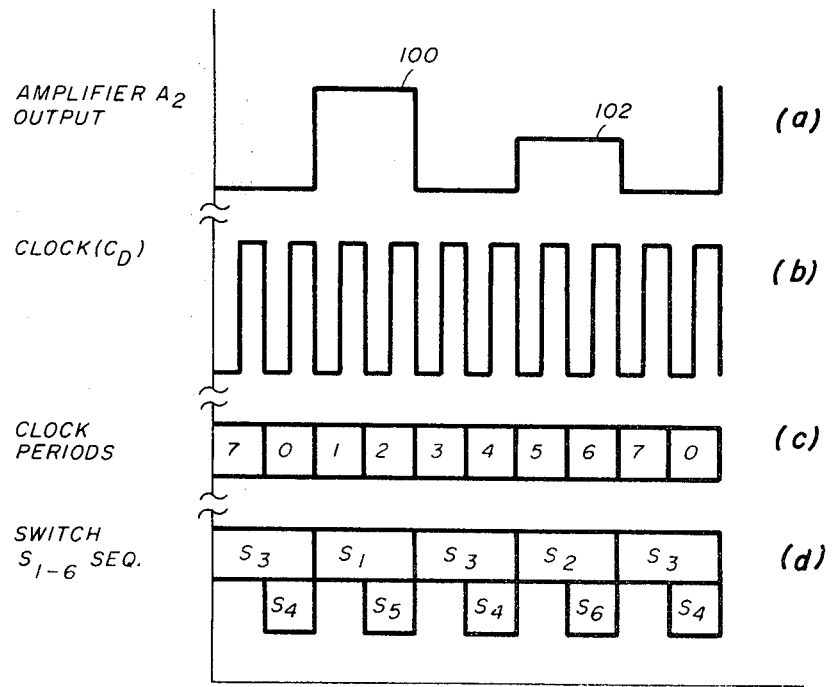

Referring for a moment to FIGS. 2 and 4, the decoder 58 provides a clock output like that shown in FIG. 4b, the corresponding output designation 0-7 inclusive, being shown at FIG. 4c. At the beginning of clock output 7, only switch $S_3$ is turned on. This provides a ground reference signal to the amplifier combinations of $A_1$ and $A_2$. During the next clock period 0, switch $S_3$ remains on and switch $S_4$ is turned on. The turning on of switch $S_4$ causes the error output voltage of amplifier $A_2$ to be stored on capacitor $C_1$. In accordance with the present invention, the storing of that output results in the correction of the inherent offset error of the amplifier circuit $A_1$ and $A_2$ by briefly closing switch $S_4$ to charge capacitor $C_1$, thereby momentarily reducing the gain of the amplifier circuit to approximately 1. When the amplifier circuit of $A_1$ and $A_2$ is subsequently called upon to amplify a signal, that amplifier is referenced to true ground.

During clock period 1, only switch $S_1$ is closed, causing the output of the reference photocells 34 to be fed into amplifier circuit $A_1$ and $A_2$. The opening of switch $S_4$ allows the amplifier circuit $A_1$ and $A_2$ to amplify that reference photocell signal (note waveform 100 in FIG. 4a) by an amplification factor determined by its design characteristics. This amplification continues as long as switch $S_1$ is closed; that is, during clock periods 1 and 2. At the beginning of clock period 2, switch $S_5$ is closed, causing the capacitor $C_{ref}$ to start charging on the output of amplifier $A_2$, through resistor $R_9$. Assuming normal clock rates, on the order of 3 – 10 Kilohertz, capacitor $C_{ref}$ does not charge completely until switch $S_5$ has cycled closed several times. However, the charging of capacitor $C_{ref}$ is completed within the 3 – 15 second period described below, with reference to the operation of switch 74 in FIG. 3.

Clock periods 3 and 4 repeat clock periods 7 and 0, conditioning the amplifier circuit $A_1$ and $A_2$ as described above. During clock periods 5 and 6, switches $S_2$ and $S_6$ are sequentially turned on, allowing the output of the cuvette photocell 30 to be amplified and stored in capacitor $C_{cuv}$ in the same manner as described above with reference to the output of the reference photocell 34 and capacitor $C_{ref}$ (note amplified cuvette photocell waveform 102 in FIG. 4a).

Refer again to FIG. 3. A period of time after $L_M$ is set, on the order of 3–15 seconds, the switch 74 is moved to the normally closed pole N/C, which returns $G_{DH}$ to its low state. $\overline{G_{DH}}$ becomes high, preconditioning $L_D$. When the output of the decoder 58 is zero, $G_{MO}$ goes high, further preconditioning $G_{LS}$. When $C_{DA}$ momentarily goes high with the falling edge of the clock pulse, $G_{LS}$ goes low setting $L_D$, which turns on switch $S_7$ and resets $L_M$. This 3 – 15 second time delay is provided to allow turbidity conditions in the blood sample to stabilize and to allow the charging of capacitors $C_{cuv}$ and $C_{ref}$ to also stabilize, as described above. It will be understood that the switching functions of switch 74, and switch 75 described below, may be made responsive to the mechanical position of the probe, or similar means, which may be used to inject the blood sample and a saline solution into the cuvette 22. A hemoglobin and red blood cell count machine manufactured by Fisher Scientific Instruments, Inc., of Pittsburgh, Pa., referred to as the Model 400 Hemalyzer, employs a mechanical probe of this type.

Refer again to FIG. 2. The turning on of switch $S_7$ connects $R_{10}$ to a voltage provided across potentiometer $R_{14}$, which is divided through resistors $R_{13}$ and $R_{12}$. This causes the charge stored on capacitor $C_{ref}$ to decrease logarithmically toward the junction of resistors $R_{13}$ and $R_{12}$. When the charge on capacitor $C_{ref}$ is drained to a level equal to the charge stored in capacitor $C_{cuv}$, the output of $C_o$ of comparator $A_5$ goes low, which snaps the NAND Schmitt trigger 72, resetting $G_{LS}$ and $L_D$, and setting $L_{EP}$. This turns off switch $S_7$ (note output $L_D$ in FIG. 3). At this point, it should be noted that the network formed by resistors $R_{12}$ and and $R_{13}$ and potentiometer $R_{14}$ provides means for adjusting the ground reference of resistor $R_{10}$, thereby allowing the discharge rates of capacitors $C_{ref}$ and $C_{cuv}$ to be altered in the event that a constant output error from amplifier $A_2$ is present.

During the period when switch $S_7$ is closed, oscillator pulses enter the register $L_{SD}$ through gate $G_D$ from $\overline{C_D}$. When switch $S_7$ is open, this oscillator pulse train is terminated and the number of pulses representative of the time required to discharge capacitor $C_{ref}$ to the level of capacitor $C_{cuv}$ is stored in the three registers 71, 73 and 77. It will be understood that resistor $R_{10}$ (FIG. 2) provides a means for adjusting the period of closure of switch $S_7$, much in the same manner as the proportionality adjustment would be made to the galvanometer 36 in FIG. 1.

Switch 75 of FIG. 3 is then closed grounding the normally open contact N/O; as noted previously, this may be accomplished manually, or automatically by detecting the lifting of a probe or the cuvette 22 (FIG. 1). Upon the closing of switch 75, $G_{DS}$ goes high, preconditioning the capacitor-resistor network of $R_{23}$, $R_{22}$, and $C_5$. Switch 75 is returned to the normally closed N/C position, causing $L_P$ to set, activating the printer control circuit 76 and printer 78. The hematocrit ratio is then read out of the three data registers 71, 73 and 77 via the decoders 79.

As noted above, an essential aspect of the present invention is the recognition that the hematocrit ratio of a diluted blood sample is directly proportional to the amount of light absorbed by the diluted sample. Stated conversely, the hematocrit ratio is proportional to the amount of light transmitted through the diluted sample as is set forth above in equation 3.

The method of determining hematocrit set forth above lends itself to electronic processing techniques as incorporated in the system described. It will be appreciated by those skilled in the medical electronics art that this system may be readily integrated with commercially available systems capable of measuring the blood indices, excepting hematocrit.

Since hematocrit is used by physicians as a diagnostic tool, it is essential that the electronically measured hematocrit be free from offset voltage errors. In the system described above, this is accomplished through the use of a reference capacitor and associated switching means to detect the offset voltage error an an output from the amplifier, and thereafter correct subsequent each amplified output by the amount of the offset error.

It will be understood by those skilled in the art that the logarithmic determination of transmission for purposes of expression (1) above is inverted in the circuit 50 of FIG. 2, thus arriving at the result of $2 - \log_{10} T$, 2 being the logarithm of 100.

APPENDIX

| Element | | Value |
|---|---|---|
| $R_1$ | = | 8.2 Kohm |
| $R_2$ | = | 1 Kohm |
| $R_3$ | = | 10 Kohm |
| $R_4$ | = | 47 Kohm |
| $R_5$ | = | 1 Mohm |
| $R_6$ | = | 4.7 Kohm |
| $R_7$ | = | 4.7 Kohm |
| $R_8$ | = | 100 Kohm |
| $R_9$ | = | 1 Kohm |
| $R_{10}$ | = | selected according to clock frequency and $C_{ref}$ |
| $R_{12}$ | = | ⎫ |
| $R_{13}$ | = | ⎬ selected according to amplifier ground referenced output |
| $R_{14}$ | = | ⎭ |
| $R_{20}$ | = | 10 Kohm |
| $R_{21}$ | = | 10 Kohm |
| $R_{22}$ | = | 10 Kohm |
| $R_{23}$ | = | 2.2 Kohm |
| $R_{24}$ | = | 10 Kohm |
| $R_{25}$ | = | 10 Kohm |
| $R_{26}$ | = | 1 Kohm |
| $R_{27}$ | = | 1 Kohm |
| $C_1$ | = | 0.1 microfarad |
| $C_{ref}$ | = | 1 to 5 dependent on clock frequency |
| $C_{cur}$ | = | see $C_{ref}$ |
| $C_5$ | = | 0.01 microfarad |
| $C_6$ | = | 0.001 microfarad |
| $S_1 - S_7$ | = | RCA CD4016 AE |
| $A_{1, 3, 4}$ | = | National Semiconductor LM-308 |
| $A_2$ | = | National Semiconductor Corporation LM-741 |
| $A_5$ | = | National Semiconductor Corporation LM-311 |
| 71, 73 and 77 | = | Texas Instruments 7490 |
| 58 | = | Texas Instruments 7442 |
| 60 | = | Texas Instruments 7490 |

I claim:

1. A system for determining the volumetric ratio of solids suspended in a liquid, comprising:
   means for passing a beam of electromagnetic energy through a sample of a liquid having solids suspended therein;
   means for measuring a characteristic representative of the amount of said energy absorbed by said sample;
   means for computing said volumetric ratio by electronically applying a proportionality factor to an output of said measuring means;
   means for passing said beam through a standard sample of said liquid having a known volumetric ratio, said measuring means further comprising means for measuring a characteristic representative of the amount of said energy absorbed by said standard liquid sample; and
   means for electronically calculating said proportionality factor as a ratio of said known volumetric ratio to the amount of said beam absorbed by said standard liquid sample.

2. The system recited in claim 1 further comprising means for diluting said liquid sample.

3. The system recited in claim 1 wherein said beam passing means comprises:
   means for holding a liquid sample container;
   said beam of electromagnetic energy comprising a source of light positioned adjacent said container-holding means such that said container is interposed in said beam;
   first means for receiving energy in said beam after having passed through a portion of said container filled with said liquids; and
   second means for receiving a light output directly from said source.

4. The system recited in claim 3 wherein said source comprises a light source complementary to said solids suspended in said liquids.

5. The system recited in claim 3 further comprising reference charge storing means coupled to said second receiving means whereby charge is stored therein corresponding to the amount of light received directly from said source.

6. The system recited in claim 5 wherein said measuring means comprises other charge storing means coupled to said first receiving means, whereby charge is stored therein corresponding to the amount of light received through said liquidfilled portion of said container.

7. The system recited in claim 6 further comprising:
   amplifying means coupled between both said charge storing means and first and second receiving means;
   first switching means interposed between said first and second receiving means and said amplifying means for alternately switching said amplifier between said receiving means; and
   second switching means coupled between said amplifying means and said two charges storing means for alternately switching said amplifying means between said two charge storing means.

8. The system recited in claim 7 further comprising stabilizing circuit means coupled to said amplifier for correcting offset voltages out of said amplifier.

9. The system recited in claim 8 further comprising sequencing means for alternatively energizing said first and second switching means and said stabilizing circuit means.

10. The system recited in claim 9 wherein said stabilizing circuit means comprises:
    a capacitor coupled to the output of said amplifying means; and
    third switching means coupled between said capacitor and the output of said amplifier.

11. The system recited in claim 10 wherein said sequencing means comprises means for energizing said third switching means prior to each energization of each of said first and second switching means.

12. The system recited in claim 6 further comprising:
    means for draining charge from said reference charge storage means; and
    means for measuring the time required for draining the difference in charge stored in said reference charge storing means with respect to said other charge storing means.

13. The system recited in claim 12 wherein said charge draining means comprises:
    an impedance; and
    means for sequentially applying said impedance across said reference charge storing means.

14. The system recited in claim 13 wherein said time measuring means comprises:
    repetitive pulsing means; and
    means for counting the number of repetitive pulses from said pulsing means during said charge difference draining time.

15. The system recited in claim 14 further comprising a comparator circuit coupled to both said charge storing means for interrupting said counting means when both said charge storing means have equal charges stored therein.

16. The system recited in claim 12 further comprising means for altering the discharge rate from said two charge storing means.

17. The system recited in claim 16 further comprising means for adjusting said correction voltage to the sum of any offset voltage out of said amplifier and any noise voltage across said charge storing means.

18. The system recited in claim 1 wherein said solid consists essentially of blood cells, and wherein said volumetric ratio comprises the hematocrit ratio of said blood cells.

19. The system recited in claim 18 wherein said measuring means comprises means for measuring the amount of said electromagnetic energy transmitted through said sample.

20. A system for determining the hematocrit ratio of blood cells suspended in a liquid, comprising:
 means for passing a beam of electromagnetic energy through a sample of said liquid having said blood cells therein;
 means for determining a characteristic representative of the amount of energy absorbed by said blood cells in said sample;
 means for storing a charge corresponding to the magnitude of said absorbed energy characteristic;
 means for storing a charge corresponding to the magnitude of energy in said beam before passing through said sample;
 means for determining the logarithm of the difference of charges stored in said two charge storing means;
 means for computing said volumetric ratio by electronically applying a proportionality factor to an output of said logarithm determining means;
 means for passing said beam through a standard blood sample having a known hematic ratio, said determining means further comprising means for determining a characteristic representative of the amount of energy absorbed by said standard blood sample; and
 means for electronically calculating said proportionality factor as a ratio of said known hematic ratio to the amount of said energy absorbed by said standard blood sample.

21. The system recited in claim 20, further comprising:
 repetitive pulsing means; and
 means for counting the number of said repetitive pulses during operation of said stored charge difference determining means.

22. The system recited in claim 21, further comprising means for providing a visual indication of the number of said repetitive pulses counted.

* * * * *